United States Patent [19]

Staniford et al.

[11] Patent Number: 5,370,990
[45] Date of Patent: Dec. 6, 1994

[54] DIAGNOSTIC ASSAY FOR FRUCTOSAMINES

[75] Inventors: Julie M. Staniford, Maidstone; John A. Power, Sevenoaks; John A. Lovelady, Maidstone, all of England

[73] Assignee: Genzyme Corporation, Cambridge, Mass.

[21] Appl. No.: 919,434

[22] Filed: Jul. 27, 1992

[30] Foreign Application Priority Data

Jul. 29, 1991 [GB] United Kingdom ............ 9116315.4

[51] Int. Cl.$^5$ .................. C12Q 1/00; C12N 1/20; C12N 1/16; G01N 33/00
[52] U.S. Cl. .................. 435/4; 435/240.27; 435/249; 435/252; 435/252.1; 435/256.1; 435/256.4; 435/255.1; 436/88; 436/87
[58] Field of Search ............ 435/4, 240.27, 249, 435/255, 252; 436/88, 87

[56] References Cited

U.S. PATENT DOCUMENTS

| | | | |
|---|---|---|---|
| 3,772,152 | 11/1973 | De Baynast | 435/249 |
| 4,797,473 | 1/1989 | Tarsio et al. | 435/240.27 |
| 4,956,301 | 9/1990 | Ismail et al. | 436/87 |
| 5,002,893 | 3/1991 | Rosenthal | 436/87 |
| 5,055,388 | 10/1991 | Vogt et al. | 435/4 |
| 5,071,767 | 12/1991 | Portenhauser et al. | 436/87 |
| 5,110,745 | 5/1992 | Kricka et al. | 436/87 |
| 5,116,762 | 5/1992 | Vogt et al. | 436/87 |
| 5,149,633 | 9/1992 | Vogt et al. | 435/4 |

FOREIGN PATENT DOCUMENTS

| | | |
|---|---|---|
| 291060 | 11/1988 | European Pat. Off. . |
| 309882 | 4/1989 | European Pat. Off. . |
| 280297 | 10/1986 | Japan . |
| 195900 | 8/1990 | Japan . |
| 155780 | 7/1991 | Japan . |

OTHER PUBLICATIONS

Horiuchi, T. et al, Agric. Biol. Chem., 55(2), pp. 333–338 (1991).
Buglova, T. T., Mikrobiol. Zh(Kiev), 45(3), 70–7.
Horiuchi, T. et al, Agric. Biol. Chem., 53 (1), pp. 103–110 (1989).
Horiuchi, T. et al, Chemical Abstracts, 108, 128107 (1988).

Primary Examiner—Michael G. Wityshyn
Assistant Examiner—Louise N. Leary
Attorney, Agent, or Firm—William G. Gosz

[57] ABSTRACT

A method for the determination of glycated protein in a sample characterised in that it comprises treating the sample with a protease and treating the protease-treated sample with a ketoamine oxidase, a product of this reaction being measured is disclosed.

9 Claims, 5 Drawing Sheets

1-Imino-1-Deoxyglucose
(Labile Schiff Base)

Amadori Rearrangement

Fructosamine

The Reaction of Glucose with Protein to form Fructosamine

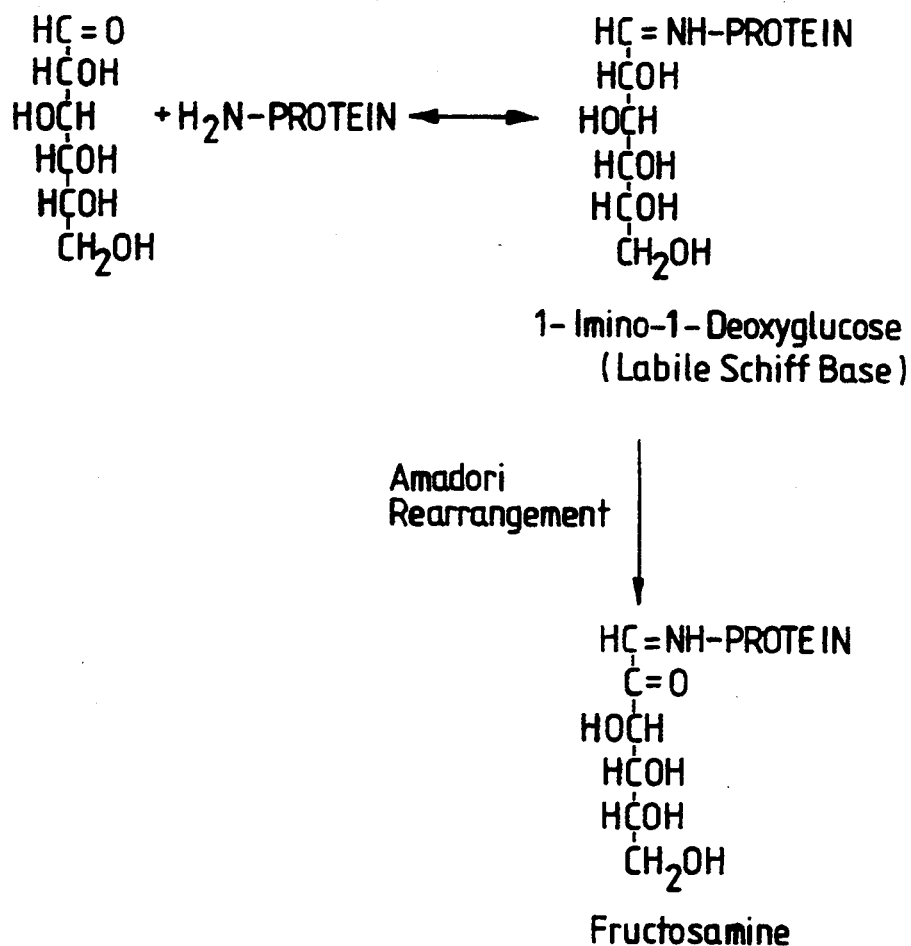
Fig.1: The Reaction of Glucose with Protein to form Fructosamine

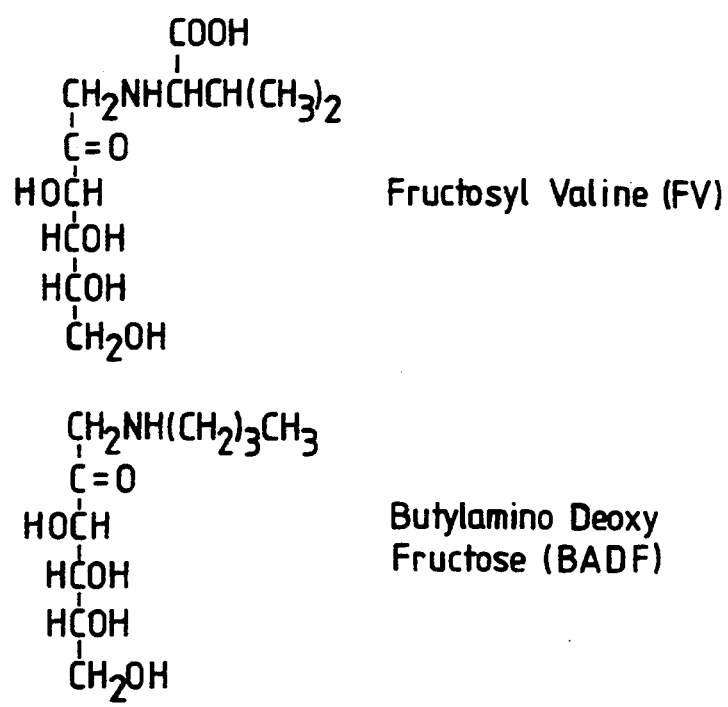
Fig.2: The Model Target Molecules, Fructosyl Valine and Butylamino Deoxy Fructose

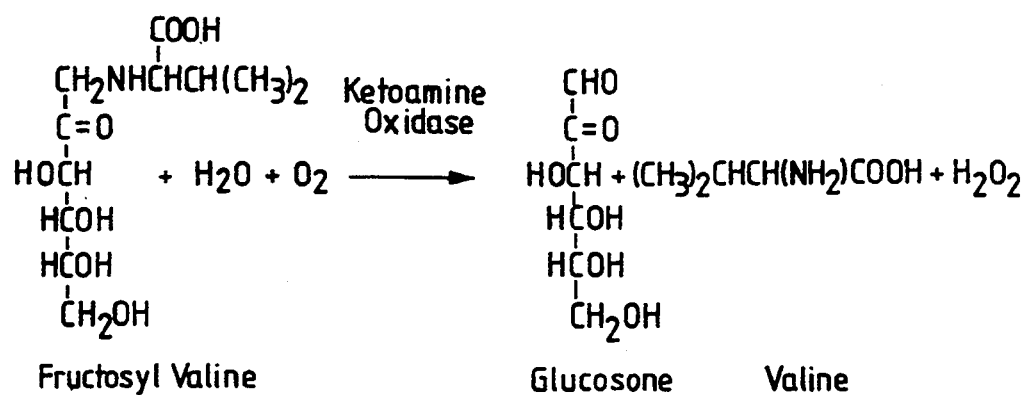
Fig. 3. Oxidation of Fructosyl Valine by Ketoamine Oxidase
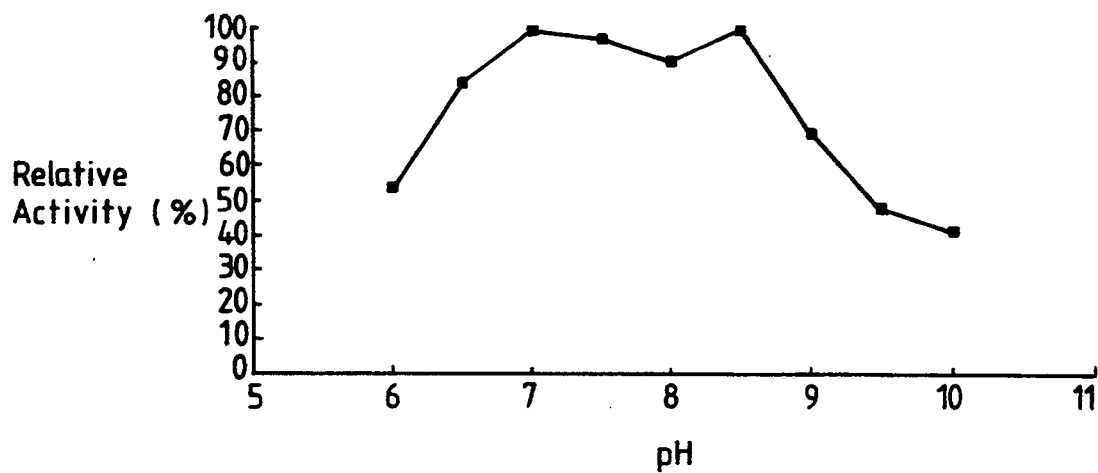

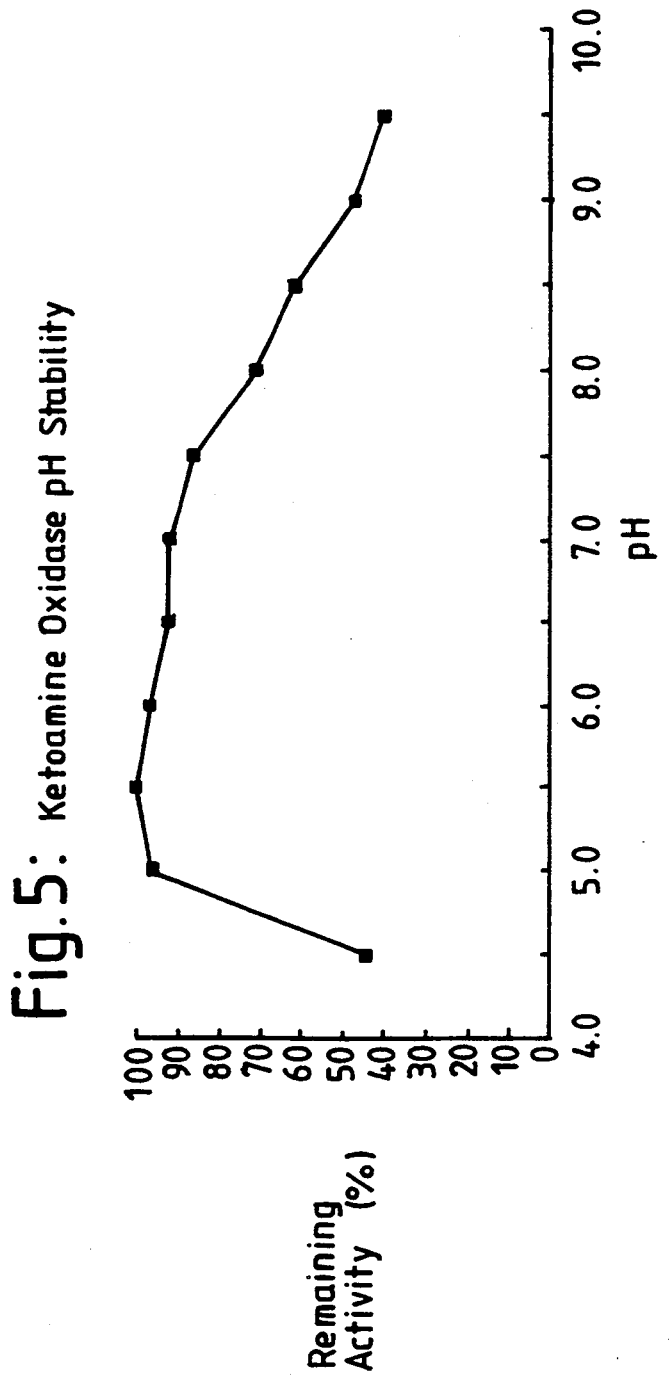
Fig. 5: Ketoamine Oxidase pH Stability

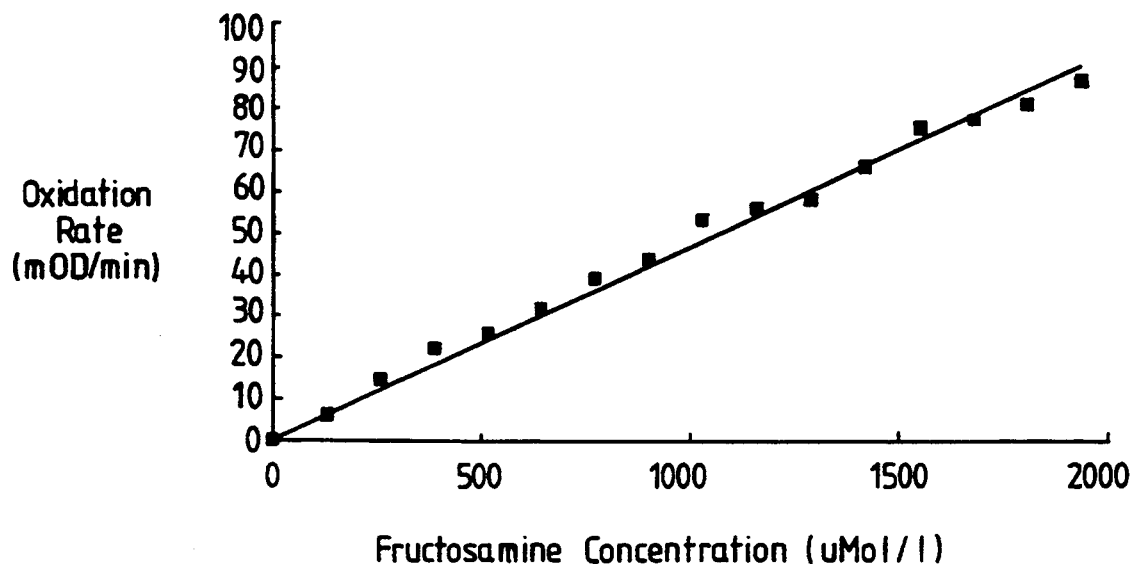
Fig.6: Fructosamine Standard Curve Kinetic Assay.
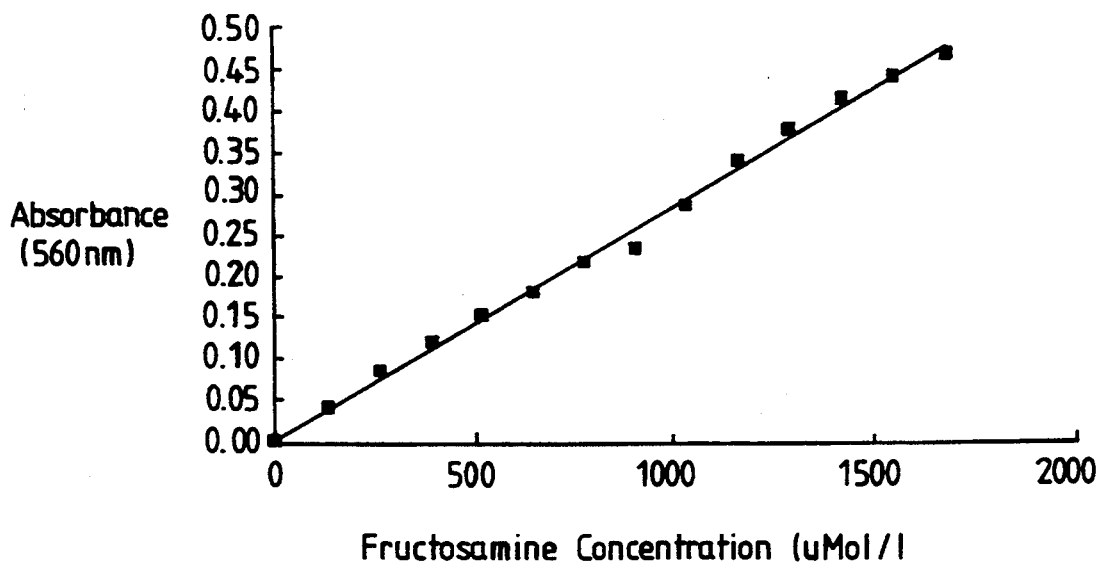
Fig.7: Fructosamine Standard Curve Endpoint Assay.

DIAGNOSTIC ASSAY FOR FRUCTOSAMINES

BACKGROUND OF THE INVENTION

This invention relates to an assay; more particularly, it relates to a method for the determination of fructosamines or other glycated proteins in biological materials.

Fructosamines are glycated proteins, present in biological materials, for example blood serum. "Glycation" is defined as the non-enzymatic glycosylation of proteins, such as serum albumin, by the condensation of reducing sugars, such as glucose, with the protein, (see Roth, M., (1983), Clin. Chem., 29, 1991). The reaction of glucose with albumin involves the nucleophilic attack of the carbonyl group of glucose on free amino groups on the protein. The thus-formed Schiff base may hydrolyse back to glucose and protein or it may undergo an Amadori rearrangement, (see Hodge, J.E., (1955), Adv. Carbohydr. Chem., 10, 169–205), to form a ketoamine structure. This reaction sequence is illustrated in accompanying FIG. 1. The Amadori compound is stabilised by equilibration of the linear ketoamine structure into several cyclic, hemiketal conformations in solution. The principal sites of glycation are the $\epsilon$-amino groups of lysine residues and the $\alpha$-amino group of the protein's terminal amino acid. Once formed, the stable ketoamine structure remains with the protein throughout its life-span.

Many disease states are characterised by unusually high or low levels of specific components of the body's metabolism. If the normal concentration range of a component in a healthy population is known then the detection of abnormal levels of this component provides a useful indication of metabolic disorder caused by disease. The purpose of clinical diagnostic tests, therefore, is to allow the performance of qualitative and quantitative analysis on body fluids, such as blood, urine and spinal fluid, as well as on tissue and other materials. The information obtained from these tests is useful to physicians in the monitoring and treatment of disease. For the information to be meaninfgul, the tests performed must be reliable and accurate. Generally, diagnostic assays make use of some unique chemical property of the analyte as the basis of the assay method. A sample of the body fluid or other material containing the analyte to be measured, generally after a suitable work-up, is contacted with a reagent which is designed to interact with the analyte in a specific way so that a measurable signal is produced. Thus, a chemical assay would involve a reagent that reacts with the analyte in a measurable way, without reacting with other components of the sample. Ideally, the reaction between the reagent and the analyte should be so specific that no other substances will react in the same manner. However, in chemical based assays, this is seldom the case and interfering side reactions are often a problem.

This problem may frequently be overcome by designing an enzyme based assay. Enzymes, by the very nature thereof, are highly specific for their substrate molecules. Although an enzyme depends on the chemical properties of its substrate to perform a specific reaction the enzyme must first recognise the physical and chemical "shape" of the substrate so that binding may occur. Only then may the enzymic reaction take place. In an enzyme based assay, therefore, a reagent containing an enzyme specific for the analyte is usually used to bind and transform the analyte in a way that is measurable. Enzyme based diagnostic assays may therefore offer advantages of specificity over chemical methods.

The level of fructosamine present in blood is governed by the concentration of sugars, such as glucose, in solution in serum. As fructosamines have a half-life of 2–3 weeks in serum, the level of fructosamine present reflects the average blood glucose levels over a period of 1–3 weeks. Thus, measurement of this parameter is a useful means of monitoring glycaemic control in diabetes mellitus.

At present, there are several established non-enzymic methods for measuring levels of serum fructosamines. For example, one method involves the separation of glycated from unglycated proteins by affinity chromatography, (see Diabetes, (1980), 29, 1044–1047).

Immobilised m-aminophenyl-boronic acid complexes with the cis-diol groups of the glycating sugars under alkaline conditions. Unbound materials are removed by washing with buffer and the fructosamines are eluted by high concentrations of sorbitol. The levels of fructosamine in the eluent may then be measured by absorbance at 280 nm or by chemical methods. The disadvantages of such a method are that free glucose must first be removed from the samples and that the amount of glycated protein that binds to the immobilised m-aminophenyl-boronic acid is critically dependant on chromatographic conditions. This may therefore reduce the accuracy of the method.

Another known method involves the detection of the breakdown products of acid hydrolysis of the ketoamine bonds. Treatment of glycated proteins with strong acids at elevated temperatures, such as 6 mol/l HCl at 95° C., causes hydrolysis of the glycated lysine residues and yields a specific product, N-(2-furoylmethyl)-L-lysine (furosine). Furosine is measured by HPLC using a reverse phase column and simultaneous UV detection at 254 and 280 nm, (see J. Clin. Chem. Clin. Biochem., (1981), 19, 81–87). Human serum albumin containing a known amount of glycated lysine residues is used for calibration. However, the method is time consuming and unsuitable for routine work or automation.

Acid hydrolysis of fructosamine is also used in another method in which treatment with weak or diluted acids yields 5-hydroxymethyl-2-furfuraldehyde. This product may be determined spectrophotometrically at 280 nm after HPLC separation. However, a more convenient method involves the reaction of the furfural product with 2-thiobarbituric acid, which results in a derivative with an absorbance maximum at 443 nm (see FEBS Lett., (1976), 71, 356–360). This procedure has been partially automated using dedicated equipment; however, the accuracy of the results depends on several factors including the level of protein in the samples, the conditions of the acid hydrolysis and the removal of glucose.

A further method which has recently replaced many of the above procedures depends on the reducing ability of fructosamine in alkaline solutions. One such method involves the addition of a serum sample to carbonate buffer, pH 10.35, containing nitroblue tetrazolium (NBT). The NBT is reduced, probably via a superoxide radical intermediate, and the absorbance of the formazan product is measured at 550 nm. The method relies on the observation that most interfering components in serum react in the first 10 minutes and hence specific serum reducing activity is measured between 10 and 15 minutes. The procedure is rapid and has been automated on a variety of analysers for clinical diagnostic use.

However, the specificity of the method for glycated proteins has been questioned and it has been shown that non-specific components may lead to interference and misinterpretation of the results. In addition, the fructosamine level is influenced by the level of albumin in the sample and so the results may need to be adjusted, especially in cases of hypoalbuminaemia.

An object of the present invention is to provide a method for measuring serum fructosamine levels as an indicator of diabetic control, for example, which offers significant advantages over the existing methods. In order to do this, it was necessary to provide enzymes capable of using glycated proteins as substrates.

SUMMARY OF THE INVENTION

The present invention provides a method for the determination of glycated protein in a sample characterised in that it comprises treating the sample with a protease and treating the protease-treated sample with a ketoamine oxidase, a product of this reaction being measured. (It is a characteristic of the present ketoamine oxidases that the reaction produces a sugar osone and hydrogen peroxide, either of which may be measured by conventional means as an indication of glycated protein content of the sample.)

Preferably, the ketoamine oxidase is obtainable from the bacterial groups Klebsiella or Corynebacterium, from the fungal genera Fusarium or Acremonium or from the yeast genus Debaryomyces; more preferably, the ketoamine oxidase is obtainable from *Debaryomyces vanrijiae* var. *vanrijiae*. Generally, a protease pre-treatment is carried out using a protease selected from proteinase K, pronase E, ananain, thermolysin, subtilisin and bovine pancreatic proteases. The protease treatment is preferably performed in the presence of a suitable detergent, in particular SDS, "Brig 35" and "Tween 20". It is commonly more convenient to measure the hydrogen peroxide involved, rather than the osone, and this may easily be done by the known Trinder method.

The present invention further provides a kit for the determination of glycated protein in a sample characterised in that it comprises a protease and a ketoamine oxidase.

The present invention also provides a ketoamine oxidase characterised in that it catalyses the oxidation of the carbon atom in position 1 of a sugar moiety of a glycated protein with consequent hydrolytic disruption of an amine bond to release a sugar osone and hydrogen peroxide from an amino acid and a process for the production thereof which comprises the use of a model substrate, preferably butylamino-deoxy-fructose (BADF), as inducer and/or screen. Preferred sources of such enzymes are as given above.

BRIEF DESCRIPTION OF THE DRAWINGS

FIG. 1 illustrates the reaction of glucose with a protein to form a Schiff base. The Schiff base may hydrolyze back to glucose and protein, or it may undergo an Amadori rearrangement to form a fructosamine.

FIG. 2 depicts two model substrates: fructosyl valine (FV) and butylamino deoxy fructose (BADF).

FIG. 3 is an illustration of the oxidation of fructosyl valine by ketoamine oxidase.

FIG. 4 is a pH/activity profile of ketoamine oxidase prepared from *Debaryomyces vanrijiae* var. *vanrijiae*.

FIG. 5 is a pH/stability profile of ketoamine oxidase prepared from *Debaryomyces vanrijiae* var. *vanrijiae*.

FIG. 6 shows the rate of reaction, measured in fructosamine concentration, of ketoamine oxidase with human serum albumin.

FIG. 7 depicts the mean absorbance and fructosamine concentration of ketosamine oxidase reacted with human serum albumin.

DESCRIPTION OF THE PREFERRED EMBODIMENTS

The present invention involves the use of such an enzyme specific for ketoamine compounds of the Amadori type. The present method, being enzyme based, has a high level of specificity for such compounds. A further advantage of the present invention is that the enzyme used is an oxidase which releases $H_2O_2$ as a byproduct of the reaction. The $H_2O_2$ released may readily be measured, preferably by means of the widely used Trinder method, (see Ann. Clin. Biochem., (1969), 6, 24–27), thus providing a method for measurement of fructosamines that is easily automated on existing autoanalysers.

The screen for the desired enzymic activities was based on well-established microbiological techniques. The selection technique depends oil the use of a defined culture medium in which the sole source of some essential atom, such as nitrogen, is supplied as the proposed target molecule or analyte. This minimal culture medium is then inoculated with a range of environmental samples. Of the many microorganisms that will be present in these samples, only those that are able to produce suitable enzymes to breakdown the target analyte will be able to release the limiting nutrient and grow. Microorganisms that grow on this medium may then be isolated and the required enzyme activity extracted.

This method is particularly suitable for use with simple or low molecular weight target molecules. However, when the target molecule is large and complex, such as fructosamine, the method is significantly less reliable. This is because in a large target molecule there may be more than one of the limiting atoms which may be released by a variety of means. For instance, if fructosamine were used, in a selective medium, as the sole source of nitrogen for growth, many microorganisms would have the ability to extract nitrogen from this molecule by means of proteolytic enzymes. Due to the abundance of nitrogen atoms in fructosamine, no selective pressure is placed on the organisms in the medium to rely on the nitrogen in the ketoamine portion of the protein for growth. This analyte is therefore unsuitable for use in selective culture media.

Thus, because of these limitations, a different approach in the design of the selective medium was used. Model target molecules were designed which closely resembled the unique ketoamine bond of the true analyte, fructosamine, yet which contained no other nitrogen atoms apart from that in the ketoamine bond itself. To liberate the nitrogen from these molecules in a culture medium would require the cleavage of the ketoamine bonds in some manner by an appropriate enzyme. Thus, any organism which grew on this medium should have, as part of its metabolic makeup, an enzyme or enzymes capable of using ketoamine groups as substrate. Once isolated, these enzymes could then be screened for ability to act on the larger fructosamine molecules.

As described earlier, the ketoamine bond of fructosamines involves glucose and the amino acid lysine. The simplest model compound for this analyte would be a glycated lysine, i.e. fructosyl lysine. However, as lysine contains two nitrogen containing amino groups, fructosyl lysine would suffer a similar disadvantage to fructosamine as sole nitrogen source in a selective medium, that is, nitrogen could be released from this molecule without necessarily breaking the target ketoamine bond. The closely related molecule, fructosyl valine (see accompanying FIG. 2), which contains a single nitrogen atom was therefore prepared as a model substrate. Fructosyl valine was prepared by a known method, (see Keil, et al, Acta. Chem. Scand., (1985), B39, 191-193). This model ketoamine compound was used as the nitrogen source in an environmental screen for ketoamine metabolising activities. A number of microorganisms capable of degrading fructosyl valine were isolated using this method.

A disadvantage of the small size of the amino acid in fructosyl valine is that the free carboxyl group of the amino acid is in close proximity to the ketoamine bond between the sugar and the amino acid. It is possible that this carboxyl group could facilitate the breakage of the ketoamine bond by promoting acid-base catalysis at the fructosyl valine ketoamine bond. As this does not occur in the target, fructosamine, a second model substrate was designed which had no reactive group close to the ketoamine bond. This second model, BADF, was again prepared by a known method, (see Micheel and Hogemann, Chem. Bet., (1960), 93, 238) and is illustrated in accompanying FIG. 2. A further microbial screen was performed using BADF as the sole source of nitrogen in a minimal medium and a number of isolates were found which were capable of oxidising ketoamine bonds. A number of the desired ketoamine oxidase enzymes, of differing characteristics, were extracted from the microbial isolates produced by the screens.

The reaction catalysed by these novel ketoamine oxidase enzymes is illustrated in accompanying FIG. 3. Such an enzyme catalyses the oxidation of the carbon atom in position 1 of the sugar moiety with a consequent hydrolytic disruption of the amine bond to release a sugar osone from the amino acid. In this oxidation reaction, oxygen acts as the electron acceptor and hydrogen peroxide is produced as a byproduct.

Preferred sources of the present ketoamine oxidase enzymes are the bacterial groups Klebsiella or Corynebacterium, the fungal genera Fusarium or Acremonium and the yeast genus Debaryomyces. Particularly good results may be obtained in accordance with the present invention when using such a ketoamine oxidase obtained from *Debaryomyces vanrijiae* var. *vanrijiae.*

*Debaryomyces vanrijiae* var. *vanrijiae* may be cultured in a single step Malt Extract Broth medium. The production of ketoamine oxidase is especially facilitated by the inclusion in the medium of a ketoamine model compound, such as fructosyl valine or BADF, as an inducer. The organism may be cultured at from 15° to 40° C. over a pH range of from 5 to 9, for example. The preferred conditions for the growth are generally 22°-28° C. and pH 6.0-8.0. Growth of the organism and production of the enzyme generally takes 1-6 days.

Alternatively, the production of such an enzyme may take place in a two-stage process. The organism may be inoculated into a nutrient-rich medium, such as Tryptone-Soya medium, so that high biomass is produced. Once maximum biomass is achieved, generally in 1-3 days, the cells may be harvested by centrifugation and placed into a minimal salts medium containing a quantity of a ketoamine model compound as inducer. The cells may be incubated in this medium to allow induction and this step may take 2-24 hours.

In one presently-preferred embodiment, the process according to the present invention for the detection of glycated proteins comprises pretreatment of the sample of glycated protein to be assayed, such as fructosamine in serum, with a proteolytic reagent containing proteases, such as proteinase K, pronase E, ananain, thermolysin, subtilisin and bovine pancreatic proteases. The predigestion may be performed in the presence of a detergent, such as sodium lauryl sulphate (SDS), "Brij 35" or "Tween 20". The pretreated sample may then be contacted with a ketoamine oxidase preparation selected from the bacterial groups Klebsiella or Corynebacterium, from the fungal genera Fusarium or Acremonium or from the yeast genus Debaryomyces.

By this means, the glycated lysine groups in the fructosamine may be liberated from the protein and may then be cleaved with the release of glucosone. A characteristic of the oxidation of glycated amino acids by the ketoamine oxidase is the stoichiometric formation of hydrogen peroxide by the enzyme. The thus-formed hydrogen peroxide may be measured enzymatically. One option is to include with the preparation of ketoamine oxidase a predetermined quantity of horseradish peroxidase and suitable chromogenic substrates for this enzyme, such as 4-amino phenazone and sodium N-ethyl-N-(2-hydroxy-3-sulphopropyl)-m-toluidine (TOOS). In this case, the hydrogen peroxide formed by the action of the ketoamine oxidase is used by the peroxidase to oxidise the chromogenic substrates.

This reaction results in colour formation in the assay mixture which may be detected by measuring the change in absorbance of the assay mixture at an appropriate wavelength. The amount of glycated protein converted may therefore be calculated by stoichiometric equivalence. Glucosone may be determined by means of aldose reagents, such as diphenylamine.

The present invention provides a diagnostic kit for the determination of glycated protein or fructosamine which is comprised of two reagents or reagent groups. One reagent group contains the protease or proteases and the detergent which is used in the pretreatment of the sample. The other reagent group contains the assay components, including the present ketoamine oxidase, which oxidises the glycated amino acids formed during the pretreatment, and the Trinder reagents, such as peroxidase, 4-amino phenazone end a phenolic or anilinic coupler used to produce a colour signal. Typically, an aliquot of the sample to be assayed is added to a suitable volume of the assay reagent. This assay mixture may be incubated at a temperature of from 10° to 60° C., more preferably from 30° to 50° C., at a pH of from 5 to 9.5, more preferably from 6 to 8, for a suitable time, usually from 2 to 20 minutes. The rate of oxidation may be measured by a kinetic or endpoint method.

The present invention provides for a new fructosamine assay which is better than existing fructosamine assays as it is based on the use of a new enzyme specific for ketoamine bonds of the type present in fructosamine. By virtue of this specificity, the present assay is generally less susceptible to interference, possibly by other substances present in blood samples than existing methods. The method may easily be adapted for use on existing automated analysers.

The present invention will be further illustrated by the following Examples:

EXAMPLE 1

Cells of a culture of *Fusarium oxysporum* (IMI 353436) were inoculated into 500ml Ehrlenmeyer flasks containing 100 ml of a medium composed of the following: glycerol (10 g/l), $Na_2HPO_4.2H_2O$ (14 g/l), KCl (0.5 g/l), $MgSO_4$ (0.5 g/l), $CaCl_2$ (0.02 g/l) and fructosyl valine (2 g/l). The shakeflask cultures were incubated at 30° C. on an orbital shaker for 4 days. After this time, the cells were harvested by centrifugation at 3500 rpm for 15 minutes. The cells were washed in 0:1 M phosphate buffer, pH 8.0, and re-centrifuged as before. The pellet was then resuspended in 0.1M phosphate buffer, pH 8.0, to 20% of the volume of the original harvest volume. Since the enzyme is located intra-cellularly in this organism, 20 ml aliquots of the cell suspension were each sonicated for 15 minutes to release the enzyme into solution. The sonicate was then centrifuged at 3500 rpm for 30 minutes to remove cell debris. The resulting enzyme solution was dialysed for 20 hours at 4° C. against two changes of 3 liters of 0.1M phosphate buffer, pH 8.0.

The activity of the preparation was assayed using the model substrate BADF. The assay mixture was prepared as follows:

200 µl enzyme preparation
40 µl horseradish Feroxidase (1.45 mg/ml)
60 µl phenol (5.5 mg/ml)
60 µl 4-aminophenazone (2 mg/ml)
720 µl 0.1M phosphate buffer, pH 7.9

This mixture was pre-incubated in a 1 ml cuvette at 37° C. and any blankrate measured by following the change in absorbance at 505 nm. 120 µl of BADF (3 mg/ml) was then added to the cuvette and the ketoamine oxidase activity measured. (One unit of activity is defined as the amount of enzyme that causes the oxidation of one micromole of BADF per minute at 37° C.) By this method, the ketoamine oxidase activity of this preparation was found to be 30 U/l.

EXAMPLE 2

A 250 ml shakeflask containing 50 ml of Tryptone-Soya medium was inoculated with cells from a culture of *Acremonium sp* (IMI 353437). This shakeflask was incubated at 30° C. on an orbital shaker for 24 hours. A 15 ml aliquot from this culture was then inoculated under aseptic conditions into a 2 liter stirred fermenter containing 1.5 liters of sterile Tryptone-Soya medium. To this fermenter, was added 350 mg/l of a BADF solution through a sterile filter. The medium was agitated at 1000 rpm and 1 l/min of air was sparged through the culture. Temperature was maintained at 28° C. throughout the fermentation.

After 96 hours the absorbance at 470 nm of the culture broth reached 12-15 optical density units and the contents of the fermenter were harvested by centrifugation at 7000 rpm for 15 minutes. The cell pellets were washed in 0.1 M phosphate buffer, pH 8.0, and then re-suspended in 250 ml of the same buffer. The cells were lysed by sonication for 25 minutes and the cell debris was reproved by centrifugation at 7000 rpm for 20 minutes. The supernatant enzyme solution was dialysed against two changes of 5 l of the phosphate buffer. Using the assay described in Example 1, this preparation was found to contain 10 U/l ketoamine oxidase.

EXAMPLE 3

A 250 ml shakeflask containing 50 ml of Malt Extract Broth was inoculated with cells from a culture of *Debaryomyces vanrijiae* var. *vanrijiae* (NCYC 2386) . The shakeflask was inoculated under aseptic conditions into a stirred fermenter containing 1.5 liters of sterile Malt Extract Broth. 0.5 g/l of BADF was added as inducer to the fermenter through a sterile filter. The medium was agitated at 1000 rpm and 1 l/minute of air was sparged through the culture. The termperature was maintained at 28° C. throughout the fermentation and the pH was controlled at 6.0.

After 24 hours growth the cells were harvested by centrifugation, washed in 50 mM phosphate buffer, pH 7.5, and then collected again by centrifugation. The cell pellet was resuspended in the same buffer to a volume of 250 ml and the slurry was sonicated to lyse the cells.

The flocculating agent, "Magnafloc LT31" (0.1%) was added to the suspension and the cell debris was removed by centrifugation. An ammonium sulphate frontcut was performed on the solution by adding solid ammonium sulphate to 40% saturation. The precipitate thus formed was removed by centrifugation and discarded. A backcut was performed by raising the ammonium sulphate concentration to 65% saturation and the precipitate was harvested. The precipitate was resuspended in 50 ml of 20 mM piperazine buffer, pH 5.5, and this solution was diafiltered on an Amicon Centriprep 30 module against the same buffer containing 0.1 mM EDTA, 0.1 mM PMSF and 0.2 mM benzamidine. After diafiltration the solution was centrifuged at 3000 rpm for 20 minutes to remove precipitate. 6 ml of the supernatant was loaded onto a Pharmacia Mono S HR5/5 column which had previously been equilibrated with the 20 mM piperazine, pH 5.5, buffer, and the ketoamine oxidase enzyme was removed from the column by isocratic elution in 15 column volumes. The fractions containing ketoamine oxidase were pooled to yield a preparation which contained 0.8 U/ml ketoamine oxidase and 83 µg/ml protein.

The Km of the enzyme prepared in this manner was determined for BADF and was found to be 80 µmolar. Accompanying FIGS. 4 and 5 show the pH/activity and pH/stability profiles of the ketoamine oxidase prepared in the above manner. The pH optimum for activity is in the range cf from 7.0 to 8.5, while the enzyme is most stable in the range of from 5 to 7.5.

EXAMPLE 4

4 g of Sigma human albumin and 5 g of glucose were dissolved in 80 ml of 50 mM phosphate buffer, pH 7.4, containing 150 mM sodium chloride. The mixture was sterile filtered into a sterile flask and incubated at 37° C. for 21 days. After this time, the solution was dialysed against 50 mM Tris/HCl buffer, pH 7.9, and then centrifuged at 3500 rpm for 20 minutes to remove any precipitate. The solution was then assayed using the Roche NBT assay and was found to contain 3880 µmol/l fructosamine.

Aliquots of this solution were diluted with 50 mM Tris/HCl buffer, pH 7.9, to produce a range of samples varying in fructosamine concentration from 0 to 1940 µmol/l. Pretreatment incubation mixtures were made up as follows for each fructosamine dilution.

190 µl Fructosamine solution
20 µl Genzyme Proteinase K (6 mg/ml)
20 µl Sigma Pronase E (6 mg/ml)

20 µl SDS (1.25%)

These mixtures were incubated at 55° C. for 30 minutes. After this time, aliquots were withdrawn from each pretreatment tube and added to the microtitre plate assay mixture as follows:

25 µl Digestion Sample
20 µl 4-amino phenazone solution (2 mg/ml)
20 µl TOOS Solution (15.5 mg/ml)
10 µl Signma Horseradish Peroxidase (1.45 mg/ml)
150 µl 50 mM Tris/HCl buffer, pH 7.9

Duplicate assays were performed for each concentration of fructosamine.

The microtitre plate was incubated at 37° C. and 25 µl of a ketoamine oxidase solution prepared as described in Example 3, with an activity of 1 U/ml, was added to each assay well. The initial rate of reaction was measured for each well for 5 minutes by absorbance charge at 560 nm. The relationship between initial rate of reaction and fructosamine concentration is shown in accompanying FIG. 6.

EXAMPLE 5

The procedure described in Example 4 was repeated, except that the ketoamine oxidase assay reaction was allowed to run to completion by incubating the microtitre plate reaction mixtures at 37° C. for 20 minutes. After this time, the absorbance of each well was measured at 560 nm. The relationship between the mean absorbance and the fructosamine concentrations obtained for this method is shown in accompanying FIG. 7.

What is claimed is:

1. A method for the determination of a glycated protein in a sample comprising the steps of:
   a) treating the sample with a protease;
   b) treating the protease-treated sample with a ketoamine oxidase obtained from a microorganism selected from the group consisting of Klebsiella, Fusarium, Acremonium, and Debraryomyces; and
   c) measuring the hydrogen peroxide product of the reaction in step (b).

2. The method of claim 1 wherein the ketoamine oxidase is obtained from Debaryomyces vanrijiae var. vanrijiae.

3. The method of claim 1 wherein the protease is selected from the group consisting of proteinase K, pronase E, ananain, thermolysin, subtilisin and bovine pancreatic proteases.

4. A method of claim 1 wherein the protease treatment is performed in the presence of a detergent.

5. The method of claim 4 wherein the detergent is selected from the group consisting of SDS, Brij 35 and Tween 20.

6. A kit for the determination of glycated protein which comprises a protease and a ketoamine oxidase, said ketoamine oxidase being obtained from a microorganism selected from the group consisting of Klebsiella, Fusarium, Acremonium, and Debraryomyces.

7. A ketoamine oxidase which catalyses the oxidation of the carbon atom in position 1 of a sugar moiety of a glycated protein with consequent hydrolytic disruption of an amine bond to release a sugar osone and hydrogen peroxide from an amino acid, said ketoamine oxidase being obtained from a microorganism selected from the group consisting of Klebsiella, Fusarium, Acremonium, and Debraryomyces.

8. The ketoamine oxidase of claim 7 which is obtained by culturing the microorganism in the presence of a model substrate.

9. A process for producing a ketoamine oxidase comprising the steps of:
   a) preparing a cell culture medium containing a microorganism selected from the group consisting of Klebsiella, Fusarium, Acremonium, and Debraryomyces, said microorganism being capable of producing ketoamine oxidase;
   b) adding fructosyl valine or butylamino deoxy fructose to the culture medium as the sole nitrogen source for said microorganism, and;
   c) obtaining ketoamine oxidase from said culture medium.

* * * * *